(12) United States Patent
Dhyllon

(10) Patent No.: US 11,377,597 B2
(45) Date of Patent: *Jul. 5, 2022

(54) ORGANIC WASTE CARBONIZER

(71) Applicant: Amen Dhyllon, Wynnewood, PA (US)

(72) Inventor: Amen Dhyllon, Wynnewood, PA (US)

(73) Assignee: SERENDIPITY TECHNOLOGIES LLC, Wynnewood, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/106,392

(22) Filed: Nov. 30, 2020

(65) Prior Publication Data

US 2022/0169926 A1    Jun. 2, 2022

(51) Int. Cl.
| | |
|---|---|
| *C10B 53/00* | (2006.01) |
| *C10B 53/07* | (2006.01) |
| *C01B 32/05* | (2017.01) |
| *B01J 31/04* | (2006.01) |
| *B01J 23/44* | (2006.01) |
| *C10B 19/00* | (2006.01) |
| *C10B 23/00* | (2006.01) |
| *C10B 57/06* | (2006.01) |
| *C12N 1/20* | (2006.01) |
| *C12R 1/38* | (2006.01) |
| *C12R 1/125* | (2006.01) |
| *C12R 1/145* | (2006.01) |

(52) U.S. Cl.
CPC ............. *C10B 53/07* (2013.01); *B01J 23/44* (2013.01); *B01J 31/04* (2013.01); *C01B 32/05* (2017.08); *C10B 19/00* (2013.01); *C10B 23/00* (2013.01); *C10B 53/00* (2013.01); *C10B 57/06* (2013.01); *C12N 1/205* (2021.05); *C12R 2001/125* (2021.05); *C12R 2001/145* (2021.05); *C12R 2001/38* (2021.05)

(58) Field of Classification Search
CPC .......... C10B 53/00; C10B 53/02; C10B 1/10; C10B 47/30; C12M 21/16; F23G 5/027; F23G 5/0273; F23G 5/0276; C10L 5/40–48
See application file for complete search history.

(56) References Cited

U.S. PATENT DOCUMENTS

| | | | | |
|---|---|---|---|---|
| 5,407,809 | A * | 4/1995 | Finn ...................... | C12M 27/10 435/41 |
| 6,802,974 | B2 * | 10/2004 | Rebholz ................. | C12P 5/023 210/603 |
| 9,284,203 | B2 * | 3/2016 | Josse ...................... | C05D 9/00 |
| 9,567,247 | B2 * | 2/2017 | Josse ..................... | C02F 11/121 |
| 11,198,819 | B1 * | 12/2021 | Dhyllon ................. | C10B 53/00 201/5 |
| 2013/0203144 | A1 * | 8/2013 | Josse ...................... | C10B 53/02 435/167 |
| 2014/0220646 | A1 * | 8/2014 | Lim ...................... | C12M 47/12 435/134 |

(Continued)

*Primary Examiner* — Jonathan Luke Pilcher
(74) *Attorney, Agent, or Firm* — Adam Warwick Bell; Matthew Rupert Kaser

(57) ABSTRACT

A method for transforming organic waste into carbon using sequential physical and biological degradation, including fermentation, drying under vacuum and elevated temperature followed by heating to a temperature of between 300° C. and 500° C. to promote carbonization and production of charcoal.

20 Claims, 3 Drawing Sheets

(56) References Cited

U.S. PATENT DOCUMENTS

2015/0027179 A1* 1/2015 Josse ................. C10B 53/02
                                                          71/10
2017/0166930 A1* 6/2017 Josse ................. C02F 11/13
2019/0002323 A1* 1/2019 Benedek ............. C10B 57/16

* cited by examiner

ORGANIC WASTE CARBONIZER

FIELD OF THE INVENTION

Conversion of organic matter such as food waste to a charcoal product ("bio-char")

BACKGROUND OF THE INVENTION

Organic wastes from leftover food and food processing is a continuing challenge. It tends to be heavy, have a high volume and moisture content, and decomposes rapidly to create an undesirable, odious and insanitary product. Large percentages of food intentionally prepared for consumption is wasted, with significant environmental and socio-economic implications. Food waste represents a significant fraction of municipal solid waste which is largely underutilized. It includes not only cooked foods but also fruit juices, seasoning and vegetables peels etc. Sustainable food waste management is urgently needed. Food waste is generated from domestic homes, hotels and restaurants and food processing plants at a rate of about 1 kg/person/day. Agricultural waste and food processing by products are produced at a larger rate. Much of this is disposed of in landfill. The high organic content is a huge potential source of energy but is currently wasted. Additionally, a vast amount of sewage waste is degraded using microbial processes which break down noxious elements, but produces large amounts of greenhouse gasses, while not harnessing the potential energy stored in the waste.

Organic waste is processed and disposed of in many ways such as microbial treatment, burying, dumping, compacting and burning. Pyrolysis and carbonization reduce volume and turn organic waste into useable fuel such as charcoal. Pyrolysis uses different kinds of biomass for biofuel production. In the process, organic by-products of agriculture and industry are converted into more valuable biofuel products such as solid char, liquid bio-oil, and syngas. Production of charcoal by carbonization has been known for centuries. Carbonization is the conversion of organic matter into low-moisture carbon substances through heating the organic matter in an environment with limited amounts of oxygen present. This process 'cracks' large molecules and is used to produce charcoal, coke, coal gas, coal tar, ammonia liquor, and "coal oil". Some current applications of carbonization are focused on conversion of biomass into biochar and syngas (synthesis gas is a fuel gas mixture consisting primarily of hydrogen, carbon monoxide, and carbon dioxide and is used in creating synthetic natural gas and for producing ammonia or methanol), and also, the conversion of waste plastics into oil, and organic chemicals into inert matter. The amount of heat applied controls the degree of carbonization and the residual content of foreign elements. For example, at 1200 K, the carbon content of the residue exceeds a mass fraction of 90 wt %, whereas at 1600 K, more than 99 wt % carbon is found. Carbonization is often exothermic, which means that it could in principle be made self-sustaining and be used as a source of energy that does not produce carbon dioxide.

BRIEF DESCRIPTION OF THE INVENTION

An object of the present invention is to provide a rapid, efficient and economical process for converting biomass into charcoal. It is a further object of the present invention to provide a pyrolytic process that is self-sustaining and, once running, does not require the input of energy from an external source. It is a further object of the present invention to reduce the required external heat input for converting biomass into charcoal. It is a further object of the present invention to provide heat energy by virtue of an exothermic pyrolytic reaction. Energy input is required to begin the reaction, but at some stage the reaction becomes exothermic and produces enough heat to be self-sustaining without the need for external energy input. In various embodiments the invention utilizes plasma contained within the carbonization chamber. A magnetic field oxygen-concentration system is used in certain embodiments. In certain embodiments, magnetic confinement may be used to contain the plasma within the carbonization chamber.

The present invention may be used to carbonize food and food-processing waste, and agricultural bio-waste such as wood, coconut shell, palm shell, rice husk, sawdust, bagasse, straw, bamboo, as well as sewage sludge. The invention encompasses a method comprising the following steps:
1) Initial biological degradation.
2) Drying under vacuum.
3) Carbonization.

These and other objects and advantages to the present invention will be readily apparent upon reference to the drawing and the following description.

DETAILED DESCRIPTION OF THE INVENTION

Figure 1:
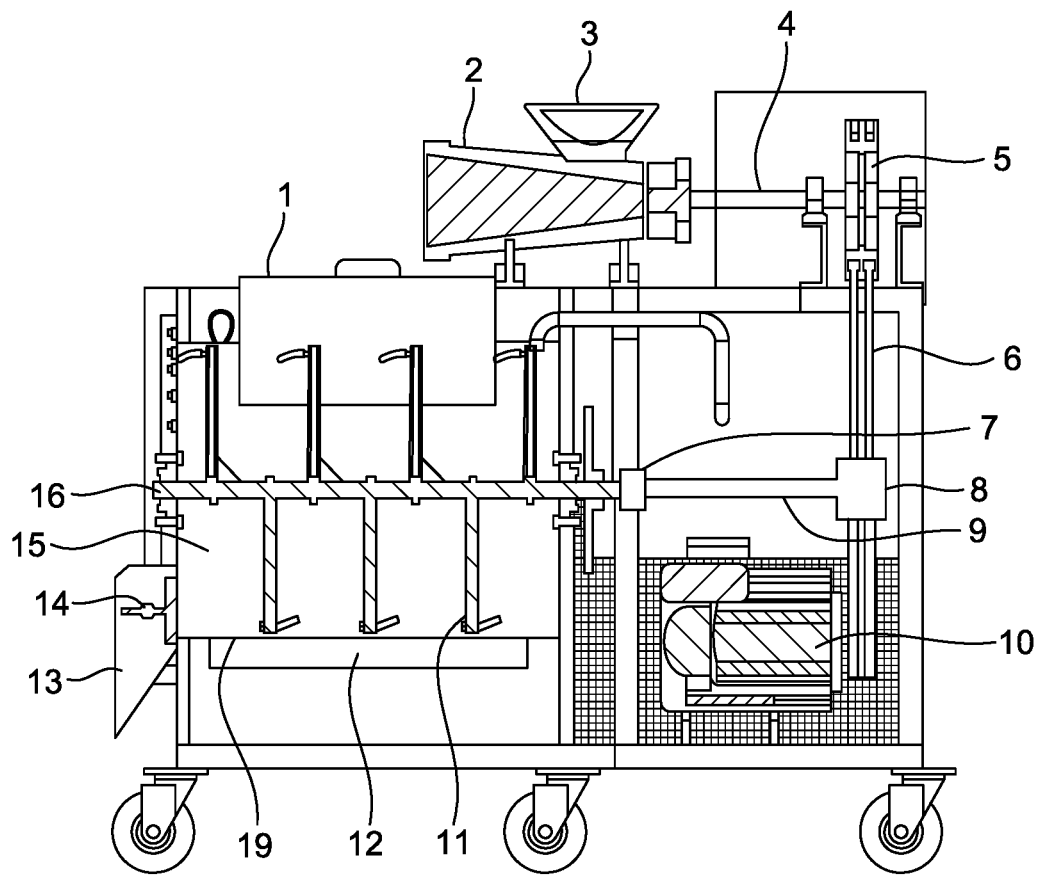
FIG. 1 Left hand side view of carbonizer machine
FIG. 2 Rear view of carbonizer machine
FIG. 3 Top view of carbonizer machine

The present solution is a high-efficiency food waste carbonization process using a carbonizer specially designed to function at a specific range of temperatures to work efficiently, with minimal energy input and designed to reduce volume and to produce charcoal that may be used as a fuel. The invention is designed to work with high-moisture materials such as food waste.

Method Embodiments

The method embodiments the invention encompasses a method comprising the following steps: 1) Initial biological degradation. 2) Drying under vacuum. 3) Carbonization.

The invention encompasses a method for carbonization comprising the following steps:
1) Initial biological degradation. This may use AEROBIC digestion and/or ANAEROBIC digestion. Place organic materials in container, and apply heat (about 37° C. to 42° C., but no higher than 46° C.).

For AEROBIC digestion, aerate and ferment with an inoculum of bacteria for a period of between 7 and 120 days at between 37° C. and 59° C. Thermophilic Aerobic Digestion (TAD) is used. Thermophilic populations to rapidly degrade carbohydrates and lipids (with loss of carbon as carbon dioxide) while accumulating N as microbial protein and the selective conservation of waste protein under appropriate digestion conditions (elevated temperature) where nitrification is unlikely to occur. The predominant thermophilic populations active in the digestion process are of the genus *Bacillus*. The majority of the thermophiles are *B. coagulans* and *B. licheniformis* with growth temperature optimal at 55° C. and growth temperature maximum not exceeding 60° C. These account for over 60% of thermophilic populations. Other participating populations were identified as *B. stearothermophilus* with growth temperature optimum at 65° C. and maximum extending up to and above 70° C.

The methods of the invention can use a multi-stage degradation using (1) *B. coagulans* and *B. licheniformis* at about 55° C.; followed by using (2) *B. stearothermophilus* at 65° C.

For ANAEROBIC digestion, the air is removed, or the container is flooded with Nitrogen, or a partial vacuum is applied. Then anaerobic digestion is carried out using an inoculum of anaerobic bacteria for a period of between 7 and 120 days. Organisms in the inoculum may include many different acetic acid-forming bacteria (acetogens) and methane-forming archaea (methanogens). *Bacillus, clostridium,* and *Enterobacter* spp are often observed along with *Methanomicrobia* and *Methanosarcina*. For example, the invention may use the potent bacterial isolates of *Bacillus subtilis* (e.g. B1U/1 and D3L/1) and *Pseudomonas* species (e.g. RAT/5). *Methanosarcina* are methanogenic Archaea and they produce valuable methane. Heat should be maintained at between 37° C. and 45° C.

The invention may employ AEROBIC digestion using (1) *B. coagulans* and *B. licheniformis* at about 55° C. (37-59C); followed by using (2) *B. stearothermophilus* at 65° C. (60-72C), all of which is done under conditions of mixing and aeration; followed by (3) ANAEROBIC digestion using one or more of *Bacillus, clostridium*, and *Enterobacter* spp are often observed along with *Methanomicrobia* and *Methanosarcina,* all of which is done under conditions of low oxygen such as vacuum, partial vacuum, or flooding with Nitrogen. ANAEROBIC organisms used may be Mesophilic, optimally around 30 to 38° C., or at ambient temperatures between 20 and 45° C., where mesophiles are the primary microorganisms present, or Thermophilic, optimally around 49 to 57° C., or at elevated temperatures up to 70° C., where thermophiles are the primary microorganisms present.

2) Drying under vacuum. After biological degradation, dry under vacuum and heat above 50° C. For example, in a preferred embodiment, heat for between 1 hour and 20 hours. Preferably heat to a temperature that does not cause combustion, but encourages drying, for example to 250° C., or between 350° C. and 450° C. E.g., 350° C. for 6 hours under partial vacuum. Vacuum is provided by a standard vacuum pump. The drying process is carried out in the same container, i.e., the carbonization chamber.

3) Carbonization. After drying, heat the interior of the food waste carbonizer to an optimum temperature between 300° C. and 500° C. to promote pyrolysis and production of charcoal. An optimal temperature for the process is 300° C. The carbonization process is catalyzed with catalyst added to the mixture of present on or on the interior walls of the carbonization chamber. For example the catalyst may be a di- or tricarboxylic acid or sulfuric acid, or may be a metal such as palladium. This process may be done under a partial vacuum (less than 1 bar, for example 0.85, 0.75, 0.5, 0.25 or 0.1 bar). Or nitrogen may be introduced to reduce oxygen in the atmosphere and increase carbonization efficiency.

The initial biological degradation step of the invention may employ biological methods for decomposition. In a preferred embodiment, the method of the invention may use *Bacillus subtilis* (e.g. B1U/1 and D3L/1) and Pseudomonas species (e.g. RAT/5). Common organic wastes can be composted using the selected isolates individually, and the C/N ratio of each substrate reduced gradually in a period of time from 1 day to 120 days. The method provides optimization of the composting process prior to drying and carbonization.

The drying step of the invention employs drying under heat and a vacuum. For example in a preferred embodiment, Heat for between 1 and 20 hours depending on temperature. Preferably heat to a temperature that does not cause combustion, but encourages drying, for example to 250° C., or between 350° C. and 450° C. E.g., 350° C. for 6 hours under partial vacuum. Vacuum is provided by a standard vacuum pump. The drying process is carried out in the same container, i.e., the carbonization chamber. In some embodiments, the reaction becomes exothermic and produces enough heat to be self-sustaining. In some embodiments the invention utilizes plasma contained within the carbonization chamber.

The Carbonization step uses heat and catalysis under vacuum or low Oxygen partial pressure to produce charcoal. The interior of the food waste carbonizer to an optimum temperature between 300° C. and 500° C. to promote pyrolysis and production of charcoal. An optimal temperature for the process is 300° C. The carbonization process is catalyzed with catalyst added to the mixture of present on or on the interior walls of the carbonization chamber. For example the catalyst may be a di- or tricarboxylic acid or sulfuric acid, or may be a metal such as palladium. This process may be done under a partial vacuum (less than 1 bar, for example 0.85, 0.75, 0.5, 0.25 or 0.1 bar). Nitrogen may be introduced to reduce oxygen in the atmosphere and increase carbonization efficiency. Other inert gasses may be used to displace the oxygen such as xenon, helium, neon, Further Methods of the Invention The invention also includes various methods of efficiently making charcoal from bio-waste. One is a method for transforming waste into carbon in a carbonization chamber, said method comprising: a) drying the waste by exposing said waste to a pressure of at least 3 bar, and a temperature of at least 250° C.; b) releasing the water vapor out of the carbonization chamber, and; c) carbonizing at least partially the waste by maintaining said waste during a period of time of at least 5 minutes to a pressure of at least 3 bar, and a temperature of at least 250° C., thereby obtaining carbon; and d) optionally separating non-organic material from the obtained carbon.

It is an objective of the present invention to provide a waste treatment process, equipment, and materials, which require a relatively small investment, low operating cost, requires minimal labor and energy. It is an objective of the present invention to provide a waste treatment process that is versatile, that can work with high moisture organic materials, and can be done in a single chamber. The process is carbon neutral and environmentally friendly and produces high quality carbon, which can be used or sold as a source of energy.

The inventor has found that combining the steps of biological degradation using specific organisms, drying under vacuum or flooded with Nitrogen, and carbonization using catalysis, very efficient carbonization occurs.

In one embodiment, rather than using a vacuum, increased gas pressure is used to increase efficiency of carbonization. In such an embodiment, air pressure inside the carbonization chamber, which is substantially air-tight in use, is increased above atmospheric pressure by use of an external pump. Pressure may be increased to, for example, 2, 3, 5, 7, 12 or 15 times atmospheric pressure. Being air-tight, all oxygen is soon combusted in the chamber, leading to increased canbonization efficiency. Additionally, Nitrogen or another inert gas may be introduced into the chamber. Other inert gasses may be used to displace the oxygen such as xenon, helium, neon, argon, or krypton.

In another embodiment, air pressure inside the carbonization chamber is decreased below atmospheric pressure by use of a vacuum pump. This reduces oxygen content, reduces combustion, and increases carbonization and charcoal production. This method is useful for large volume carbonization chambers.

In another embodiment, nitrogen is concentrated within the carbonization chamber. It may be vented in from an external nitrogen source, such as bottled gas, or it may be concentrated by use of magnets or electro-magnets placed in proximity to the air inlets, which magnets or electro-magnets will create a paramagnetic effect and concentrate the atmospheric oxygen which can be vented away from the chamber, increasing the proportion of Nitrogen.

In one embodiment, rapid removal of moisture is achieved by using a vacuum created within the carbonization chamber. This is particularly useful with slurries and effluent waste carbonization.

In one embodiment, plasma is created from air within the carbonization chamber by subjecting the air to sufficient electrical energy so that plasma is created. A plasma with a temperature as low as 5 eV can have a sufficient number of electrons above 15.6 eV to produce a weakly ionized plasma. This corresponds to about 55,000 degrees Kelvin.

Plasma may be produced by use of a plasma arc torch under an inert gas atmosphere (usually Helium or Argon) at a pressure range between 400-1,200 mbar abs. The plasma arc torch creates temperatures well above 15,000 K.

In one embodiment, efficiency of combustion and chemical breakdown is increased by providing electrical discharges within the carbonization chamber using electrodes placed inside the chamber. The electrodes are positioned to extend from the outside of the carbonization chamber to the inside and may be made of graphite to prevent contamination of the carbon product. However, at suggested operating temperatures electrodes of steel, platinum or other like compounds may be used. An electric current may be introduced by use or a ring electrode or brushes making contact with the electrodes on the outside of the carbonization chamber.

In one embodiment, efficiency of chemical breakdown is increased by using microwave radiation, or UV radiation or x-ray radiation within the carbonization chamber.

In one embodiment high pressure air jets are placed within the carbonization chamber to increase particularization of the contents and increase efficiency of combustion and chemical destruction.

In one embodiment, grinding plates and/or venturi mixing is used to grind and mix the contents of the carbonization chamber to increase breakdown of contents.

In one embodiment high pressure jets of an air/sand mixture are used within the carbonization chamber to increase structural breakdown.

In another embodiment lime, alkali and other caustic substances are introduced into the carbonization chamber to speed up chemical breakdown. Chlorins and other oxidizing substances may also be used.

In various embodiments a combination of heat and pressure may be used to speed up decomposition.

In a preferred embodiment, the carbonization chamber is air-tight or substantially air-tight when in use. This prevents oxygen entering the chamber and increases efficiency of carbonization.

In other embodiments the carbonization chamber includes vents that can allow gasses to enter or exit the carbonization chamber.

In some embodiments an exhaust vent is present that allows exhaust gasses to exit the device. In various embodiments, activated carbon can be used in the exhaust path to capture odors produced during the process. In other embodiments a condenser is used to convert gasses into bio-oil.

Preferred Method of the Invention

1) Initial biological degradation. Place organic materials in container, and heat, aerate and ferment with an inoculate of bacteria, for a period of between 1 and 120 days. For example, the invention may use the potent bacterial isolates of *Bacillus subtilis* (e.g. B1U/1 and D3L/1) and *Pseudomonas* species (e.g. RAT/5). Heat should be maintained at between 25° C. and 45° C. Centigrade. Constant aeration may be achieved by rolling in a drum. The drum may be the same drum as the carbonization chamber.

2) Drying under vacuum. After biological degradation, dry under vacuum and heat. For example In a preferred embodiment, Heat for between 15 minutes and 20 hours depending on heat used. Preferably heat to a temperature that does not cause combustion, but encourages drying, for example to 250° C., or between 350° C. and 450° C. E.g., 350° C. for 6 hours under partial vacuum. Vacuum is provided by a standard vacuum pump. The drying process is carried out in the same container, i.e., the carbonization chamber.

3) Carbonization. After drying, heat the interior of the food waste carbonizer to an optimum temperature between 300° C. and 500° C. to promote pyrolysis and production of charcoal. An optimal temperature for the process is 300° C. The carbonization process is catalyzed with catalyst added to the mixture of present on or on the interior walls of the carbonization chamber. For example the catalyst may be a di- or tricarboxylic acid or sulfuric acid, or may be a metal such as palladium. This process may be done under a partial vacuum (less than 1 bar, for example 0.85, 0.75, 0.5, 0.25 or 0.1 bar). Nitrogen may be introduced to reduce oxygen in the atmosphere and increase carbonization efficiency.

The carbonization step may also be performed under pressure, where the temperature reaches 350 to 450° C., even up to 500° C., and the pressure is at least 3 bar, preferably 8 bar, more preferably 9 bar or more. A flash point is reached and the molecules that make up the waste material are cracked to transform the waste into carbon. As long as the temperature and the pressure are maintained at the required levels, the carbonization process starts and takes from 5 to 35 minutes.

In an alternative embodiment, in the carbonization step to remove moisture, sodium borohydride powder and helium gas may be injected into the carbonization chamber. The sodium borohydride reacts with the water inside the carbonization chamber, thereby generating hydrogen.

The invention includes the following exemplary embodiments:

A method for transforming waste into carbon in a carbonization chamber, said method comprising:
providing a carbonization chamber,
loading the carbonization chamber with carbon-based waste materials, and
  (a) performing biological degradation by adding an inoculum of bacteria to the waste materials, mixing and applying heat between 37° C. and 46° C., and aerating the mixture to promote fermentation for a period of between 7 and 120 days, followed by (b) drying the contents of the carbonization chamber under at least a partial vacuum, at a heat above 50° C. for between 1 hour and 20 hours, followed by (c) heating the interior of the carbonization chamber to a temperature of between 300° C. and 500° C. to promote carbonization and production of charcoal.

As above, wherein the inoculum comprises *Bacillus subtilis* and *Pseudomonas* species, and where heat is maintained at between 37° C. and 45° C. with constant aeration.

As above, wherein the inoculum comprises *Bacillus subtilis* B1U/1 and *Bacillus subtilis* D3L/1) and *Pseudomonas* RAT/5.

As above, wherein in step (b) the heat is maintained at between 250° C. and 450° C. for between 6 hours and 18 hours, under partial vacuum.

As above, wherein in step (b) the heat is maintained at between 300° C. and 400° C. for between 6 hours and 12 hours, under partial vacuum.

6. The method of claim 1 wherein the carbonization step in (c) is catalyzed with catalyst added to the mixture or present on the interior walls of the carbonization chamber.

As above, wherein the catalyst is selected from a group consisting of: a dicarboxylic acid, a tricarboxylic acid, sulfuric acid, or a metal catalyst.

As above, wherein the catalyst comprises palladium.

As above, wherein the catalyst comprises tricarboxylic acid mixed into the mixture and palladium attached to the inside of the carbonization chamber.

As above, wherein the partial vacuum is less than 0.5 bar.

As above, wherein the partial vacuum is less than 0.1 bar.

As above, wherein, in step (c), nitrogen is introduced into the carbonization chamber to reduce oxygen in the atmosphere and increase carbonization efficiency.

As above, 1 wherein in step (c) pressure is increased in the carbonization chamber to be greater than atmospheric pressure.

As above, wherein the pressure in step (c) is at least 3 bar.

As above, wherein step (c) further comprises flooding the carbonization chamber with one of nitrogen xenon, helium, neon, argon, or krypton.

As above, wherein step (c) further comprises introducing a plasma into the carbonization chamber.

As above, wherein in step (c) the temperature is about 40,000K to 60,000K.

As above, wherein step (c) further comprises introducing an electrical discharge within the carbonization using electrodes placed inside the chamber.

As above, wherein step (c) further comprises introducing at least one of microwave radiation or UV radiation within the carbonization chamber.

As above, wherein step (c) further comprises introducing high pressure air jets into carbonization chamber to increase particularization of the contents and increase efficiency of combustion and chemical destruction.

Device Embodiments

The invention also encompasses a device, which is the food waste carbonizer of the invention, in which food waste is carbonized, ground and briquetted to form solid fuel that has commercial value for example as a fuel for cooking, barbequing, hot water production, boiler fuel etc. The Carbonizer machine in an exemplary embodiment has a 25 kg/cycle capacity, suitable for commercial kitchens. The device is a carbonization chamber comprising a filling hopper (1) for providing feedstock to the carbonization chamber. This carbonization chamber (2) includes a drum (3), a lid (4) and a floor (5) configured to contain organic waste for conversion into charcoal, and impellers (6) in the drum connected to a central rotating shaft (7) to agitate the contents, and an outlet (8) for collecting charcoal from the carbonization chamber. In a preferred embodiment, the interior of the carbonization chamber (2) is coated with retractile coating and/or catalytic materials of, for example, graphite and/or zirconia oxide, to minimize heat loss and increase efficiency of conversion of organic waste to charcoal with minimal heat input. This increases the output yield by at least 20% compared with a carbonization chamber not coated with graphite and/or zirconia oxide. The carbonizer may be run at any temperature above 250° C., such as 300° C., 400° C., 500° C., 600° C., 700° C., 800° C. or between 900 and 1500° C. Between temperature of 230° C. and 250° C., depolymerizations take place and long chain polymers are broken into short chain of hydrocarbons. Running the food waste carbonizer at an optimum temperature between 300° C. or 500° C. promotes pyrolysis and produces an optimum charcoal yield. Depending on the time of exposure and type of waste, and temperature between 300° C. and 500° C. is considered optimal for certain embodiments, and efficiency or carbonization. At lower pyrolysis temperatures (300° C.) the process converts up to 90 wt % of the original organic solids to charcoal.

In a specific, preferred embodiment, the invention (the Food Waste Carbonizer) is the machine as shown in FIGS. 1-6. The target temperature within the carbonization chamber (2) is 300° C. The carbonization chamber is coated with a refractile mixture of graphite and zirconia oxide.

The carbonizer structure of the machine is as follows. A Carbonizer machine comprising a filling hopper (3) optionally with a grinder (2) driven via a shaft (4) by a motor (10), controlled by a gear mechanism (5), and housed within a motor housing, wherein the shaft is powered via a belt drive (6) which also turns a second shaft (9) rotatably set in one or more ball-race collars (7 and 9) set in a frame, which is housed within a shaft housing, a carbonization chamber (15) comprising a hollow cylindrical sealable drum (19), with insulated walls and a lid (1) allowing access to the drum (15), configured to contain organic waste for conversion into charcoal. Within the drum is a rotating shaft (16) with impellers (11) to agitate the contents, and an outlet (13) optionally with a gate, for discharging carbonized material, clinker and collecting charcoal from the carbonization chamber. A vent (14) is provided to vent gasses or fluids, and a heater element (12) is also provided. Optionally the unit is supported by wheels to make it portable.

Figure 2:
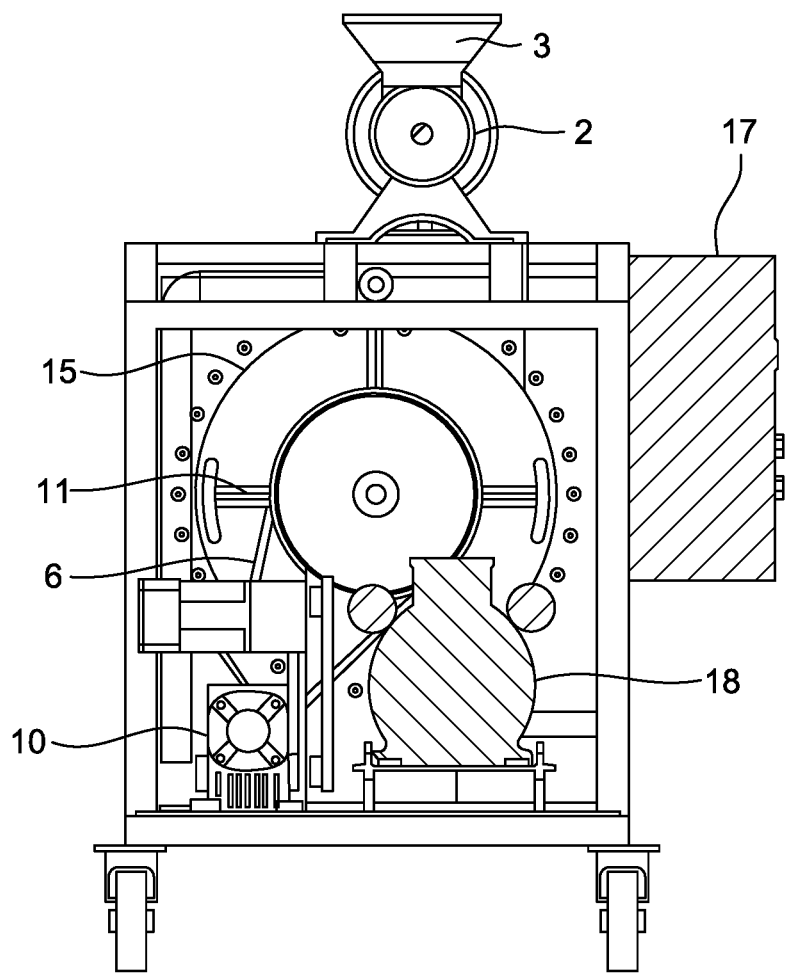
Figure 3:
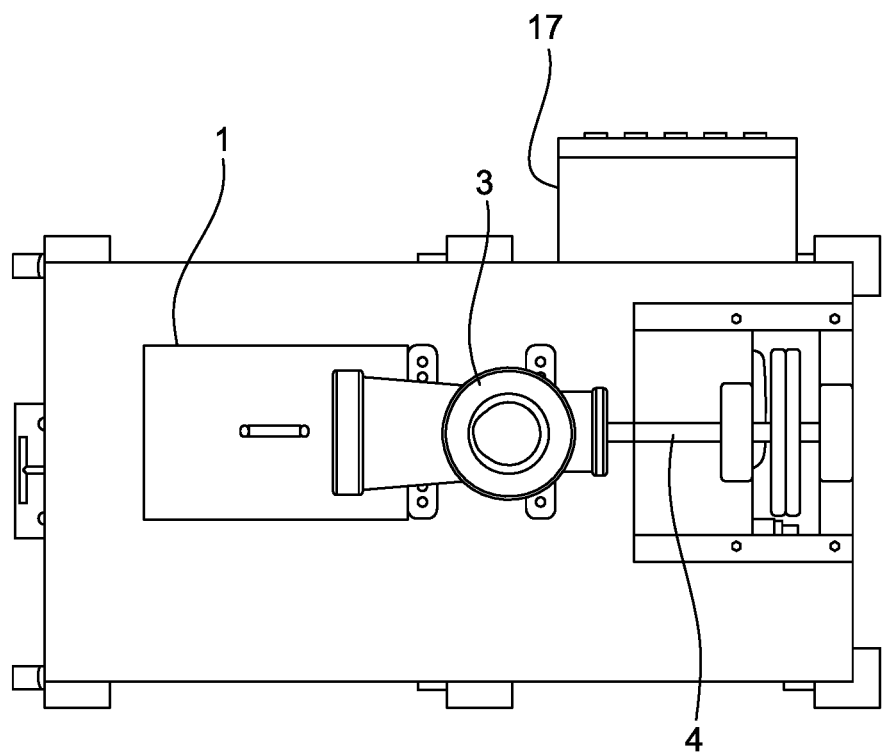

Running the food waste carbonizer at an optimum temperature between 300° C. or 500° C. promotes pyrolysis and produces an optimum charcoal yield. At 300° C., the molecular bonds between carbon and other elements such as oxygen and hydrogen are broken and carbon char is produced Operational parameters for this embodiment are:
Capacity: 50 kg-1000 Kg/day
Per load: 5 hours (1 hour cooling)
Material: Kitchen waste (Organic/Degradable)
Heating: 3 kW (Heating system: Heater band)
Process time: 5 hours, operating temperature
Power: 280-300° C., Single phase
Electrical consumption: 3 kWh FIGS. 1-3 illustrate various aspects of the Food Waste Carbonizer. It is not limited to the one shown in the figures. Variations are also contemplated as being within the scope of the claims, as will be readily apparent to those having ordinary skill in the art after becoming familiar with the teachings herein. In the example, the carbonization chamber includes a cylindrical drum comprised of walls and bottom coated with a refractile mixture of graphite and zirconia oxide. The drum includes an openable lid. The lid has a planar circular shape which allows a relatively close fit of lid with the drum walls. A lid collar may be provided surrounding a central opening in lid. The drum includes a wall formed generally as a cylinder having top and bottom ends and is coated in the inside with a refractile material such as a mixture of graphite and zirconia oxide. In an example, the drum walls may be constructed of a plurality of individual pieces. For example, two half-shells may be joined together during carbonization chamber assembly. In such an example, the pieces may be joined according to a process appropriate for the material of construction of the pieces. For example, if walls are formed of metal, the pieces may be welded together. Vents (pipes, air inlets) may be provided to extend through the drum walls between exterior and interior sides to provide inlets for accepting limited airflow into the carbonization chamber. Air vents allow outside air to enter the burn chamber and feed the fire. An external damper and/or blower pipes may be attached to the vents. A constant speed blower may be provided at the outside end of the damper pipe that provides forced air that's varied by the damper and/or computer controller. In another example, a variable speed blower may be used without a damper. In yet another example, a damper may be used without any blower. Vents, in some embodiments, may also be used to pull a vacuum from the chamber or to introduce inert gasses such as nitrogen. Vents, in some embodiments, may also be used introduce catalysts or biological materials such as bacteria and fungi for the biological degradation stage of the process.

Exemplary Method of the Invention

A method for transforming waste into carbon in a carbonization chamber, said method comprising: providing a carbonization chamber, loading the carbonization chamber with carbon-based waste materials, and (a) performing biological degradation by adding an inoculum of bacteria comprising *Bacillus subtilis* and/or *Pseudomonas* species and/or *Saccharomyces cerevisiae* to the waste materials and mixing, then applying heat between 37° C. and 46° C., and continuing to mix and aerate the mixture to promote fermentation for a period of between 6 hours and 12 hours, followed by (b) drying the contents of the carbonization chamber under at least a partial vacuum (at least 0.5 bar or below) and/or low oxygen (may be flooded with $N_2$) for between 1 hour and 20 hours, at a heat of between 50° C. and $250° C. followed by (c) heating the interior of the carbonization chamber to a temperature of between 300° C. and 500° C. to promote carbonization and production of charcoal. The carbonization step in (c) is catalyzed with catalyst added to the mixture or present on the interior walls of the carbonization chamber. The catalyst is selected from a group consisting of: a dicarboxylic acid, a tricarboxylic acid, sulfuric acid, or a metal catalyst and may comprise palladium. The catalyst may comprise tricarboxylic acid mixed into the mixture and palladium attached to the inside of the carbonization chamber. In step (c), nitrogen may introduced into the carbonization chamber to reduce oxygen in the atmosphere and increase carbonization efficiency, and pressure may be increased in the carbonization chamber to be greater than atmospheric pressure. The pressure in step (c) may be at least 3 bar.

The invention may employ AEROBIC digestion using (1) *B. coagulans* and *B. licheniformis* at about 55° C. (37-59C); followed by using (2) *B. stearothermophilus* at 65° C. (60-72C), all of which is done under conditions of mixing and aeration; followed by (3) ANAEROBIC digestion using one or more of *Bacillus, clostridium*, and *Enterobacter* spp are often observed along with *Methanomicrobia* and *Methanosarcina*, all of which is done under conditions of low oxygen such as vacuum, partial vacuum, or flooding with Nitrogen. ANAEROBIC organisms used may be Mesophilic, optimally around 30 to 38° C., or at ambient temperatures between 20 and 45° C., where mesophiles are the primary microorganisms present, or Thermophilic, optimally around 49 to 57° C., or at elevated temperatures up to 70° C., where thermophiles are the primary microorganisms present.

In step (c) the carbonization chamber can be flooded with one of nitrogen xenon, helium, neon, argon, or krypton.

In step (c) the carbonization chamber may have a plasma introduced into it for example by use of a plasma arc torch under an inert gas atmosphere of Helium or Argon at a pressure range between 400-1,200 mbar abs, creating temperatures in the chamber of above 15,000 K.

In step (c) an electrical discharge can be introduced within the carbonization using electrodes placed inside the chamber. Other things that can be used include microwave radiation or UV radiation within the carbonization chamber or high pressure air jets to increase particularization of the contents and increase efficiency of combustion and chemical destruction.

After the carbonization step, the invention may additionally use an "activation" step in which heating continues to 800° C. in superheated steam to remove the tar. The product of this stage has a very large pore volume making it most suited for adsorption and purification applications. This is done by heating the already made charcoal to 800° C. in a superheated steam atmosphere. This superheated steam performs two major functions during the activation process. The first is to isolate the charcoal from the oxidative environment ensuring that it does not burn. The second is to remove the tarry residue which is blocking the finely structured pores inside the charcoal. After this steam heating, the product must be cooled in a non-oxidative environment then stored in an airtight container. This activation process makes the inner pores in the charcoal more accessible for adsorption. It also increases the pore surface area which gives the activated charcoal excellent adsorption capacity.

Additionally, a hydrogenation step may be performed in which hydrogen gas or liquid hydrogen is contacted with the product produced by step (c). This displaced any remaining oxygen and hydrogenates the remaining double bonds.

Exemplary Device of the Invention

The device of the invention includes the following components:
The carbonization chamber can be made out of anti-rust metal, like stainless steel, preferably of cylindrical shape, which is a container that can withstand the heating and pressure conditions of the invention. The chamber is coated with refractile materials.
An agitator system to mix the materials inside the carbonization chamber.
A heating system or mechanism which can be powered from different energy sources, such as but not being limited to, electricity, gas, fuel oil, the carbon generated by the machine itself or other ways. Sufficient heat may be in the order of 1000 to 5000 W, preferably around 2000 W;

A compressor and/or vacuum system, for example a compressor, which can ensure a working pressure of at least 5 down to 0.25 bars.

A catalytic composition, which may be painted onto the internal walls of the chamber or introduced into the chamber.

An inlet to supply or inject gasses, remove gasses or introduce catalysts or biological materials to aid in digestion and degradation.

A dispensing port from which to extract the product.

An outlet to release the water vapour or gas generated inside the carbonization chamber;

An activated charcoal filters to remove the undesirable compounds and odors.

A doors through which to fill the chamber with materials and extract the resulting carbon.

Definitions

The invention has been described in this disclosure. However, it should be understood that this invention may take many different forms and thus should not be construed as being limited to the embodiment set forth herein. All publications mentioned herein are incorporated by reference for all purposes to the extent allowable by law. In addition, in the figures, identical numbers refer to like elements throughout. Additionally, the terms "a" and "an" as used herein do not denote a limitation of quantity, but rather denote the presence of at least one of the referenced items. The claims, disclosure and drawings of the present invention define but are not intended to limit the invention. All patents and publications disclosed herein are incorporated by reference to the fullest extent permissible by law.

In this disclosure, "Charcoal" is describes as a carbonaceous solid with a fixed-carbon content of 70 wt % or more. The term "biomass" includes all sorts of woody and herbaceous plant material, such as wood logs, slabs, chips, and bark; and agricultural residues such as corncobs, corn stover, wheat straw, nutshells, and sugar cane bagasse. Biomass may also include the organic fraction of municipal solid wastes, sewage sludge, manure, or other excrement, and the residues of animal husbandry, such as bones and carcasses. The term "inert" in the context of the present invention means that such compound, composition or material does not react with biomass, or its byproducts of pyrolysis, at temperatures and pressures attained within the reaction container in the practice of the present invention.

The invention claimed is:

1. A method for transforming waste into carbon in a carbonization chamber, said method comprising:
   providing a carbonization chamber having an interior that is air-tight and sealable, and loading the carbonization chamber with organic waste materials;
   then performing aerobic digestion upon the organic waste materials within the carbonization chamber, with a first mesophilic aerobic inoculum at between 45° C. and 55° C. performed with constant mixing and aeration; followed by thermophilic aerobic digestion with a second aerobic inoculum at between 55° C. and 65° C. performed with constant mixing and aeration; followed by anaerobic digestion with an anaerobic inoculum at temperatures varying between 20° C. and 57° C., performed under conditions of low oxygen;
   then drying organic waste materials within the carbonization chamber under at least a partial vacuum, at a temperature of at least 200° C.; and
   then in a final carbonization step, heating the interior of the carbonization chamber to a temperature of between 300° C. and 800° C. so as to result in the carbonization of the biologically degraded and dried organic waste material inside the carbonization chamber.

2. The method of claim 1, wherein the first mesophilic aerobic inoculum comprises *B. coagulans* and *B. licheniformis*; the second aerobic inoculum comprises *B. stearothermophilus*, and the anaerobic inoculum comprises one or more of *Bacillus, Clostridium, Enterobacter Methanomicrobia* and/or *Methanosarcina* species.

3. The method of claim 2, wherein the first mesophilic aerobic inoculum further comprises *Bacillus subtilis* B 1U/1 and *Bacillus subtilis* D3L/1) and Pseudomonas RAT/5.

4. The method of claim 1 wherein, in the final carbonization step, the temperature is maintained at between 250° C. and 450° C. for between 6 hours and 18 hours, under partial vacuum.

5. The method of claim 4 wherein, in the final carbonization step, the temperature is maintained at between 300° C. and 400° C. for between 6 hours and 12 hours, under partial vacuum.

6. The method of claim 1, wherein the final carbonization step is catalyzed with a catalyst added to the biologically degraded and dried organic waste material inside the carbonization chamber.

7. The method of claim 6, wherein the catalyst is selected from a group consisting of: a dicarboxylic acid, a tricarboxylic acid, sulfuric acid, and a metal catalyst.

8. The method of claim 6, wherein the catalyst comprises palladium.

9. The method of claim 6, wherein the catalyst comprises tricarboxylic acid mixed into the biologically degraded and dried organic waste material in the interior of the carbonization chamber, and a palladium catalyst attached to the interior of the carbonization chamber.

10. The method of claim 5 wherein, in the final carbonization step, the partial vacuum is less than 0.5 bar.

11. The method of claim 5 wherein, in the final carbonization step, the partial vacuum is less than 0.1 bar.

12. The method of claim 1, wherein, in the final carbonization step, nitrogen is introduced into the carbonization chamber to reduce oxygen in the carbonization chamber, and thereby increase carbonization efficiency.

13. The method of claim 1, wherein, in the final carbonization step, pressure is increased in the carbonization chamber to be greater than atmospheric pressure.

14. The method of claim 3, wherein, in the final carbonization step, the pressure is at least 3 bar.

15. The method of claim 1, wherein, in the final carbonization step, the carbonization chamber is flooded with one of nitrogen, xenon, helium, neon, argon, or krypton.

16. The method of claim 1, wherein, in the final carbonization step, a plasma is introduced into the carbonization chamber.

17. The method of claim 16, whereby the plasma is introduced by use of a plasma arc torch under an inert gas atmosphere of Helium or Argon.

18. The method of claim 1, wherein, in the final carbonization step, an electrical discharge is introduced within the carbonization chamber using electrodes placed inside the chamber.

19. The method of claim 1 wherein, in the final carbonization step, at least one of a microwave radiation or a UV radiation is introduced within the carbonization chamber.

20. The method of claim 1 wherein, in the final carbonization step, high pressure air jets are introduced into carbonization chamber to increase particularization of the biologically degraded and dried organic waste material inside the carbonization chamber.

* * * * *